US012661375B2

(12) United States Patent
Huppertz et al.

(10) Patent No.: US 12,661,375 B2
(45) Date of Patent: Jun. 23, 2026

(54) NUTRITIONAL COMPOSITION

(71) Applicant: FrieslandCampina Nederland B.V., Amersfoort (NL)

(72) Inventors: Thom Huppertz, Wageningen (NL); Christina Josephina Antonia Maria Timmer-Keetels, Wageningen (NL); Roelof Bos, Wageningen (NL); Jeroen Margot Leon Heck, Wageningen (NL)

(73) Assignee: FrieslandCampina Nederland B.V., Amersfoot (NL)

( * ) Notice: Subject to any disclaimer, the term of this patent is extended or adjusted under 35 U.S.C. 154(b) by 843 days.

(21) Appl. No.: 17/613,799

(22) PCT Filed: May 26, 2020

(86) PCT No.: PCT/EP2020/064498
§ 371 (c)(1),
(2) Date: Nov. 23, 2021

(87) PCT Pub. No.: WO2020/239722
PCT Pub. Date: Dec. 3, 2020

(65) Prior Publication Data
US 2022/0211763 A1    Jul. 7, 2022

(30) Foreign Application Priority Data

May 27, 2019    (EP) ..................................... 19176789

(51) Int. Cl.
| | |
|---|---|
| *A61K 35/20* | (2006.01) |
| *A61K 9/16* | (2006.01) |
| *A61K 31/702* | (2006.01) |
| *A61P 1/14* | (2006.01) |

(52) U.S. Cl.
CPC ............ *A61K 35/20* (2013.01); *A61K 9/1617* (2013.01); *A61K 31/702* (2013.01); *A61P 1/14* (2018.01)

(58) Field of Classification Search
CPC combination set(s) only.
See application file for complete search history.

(56) References Cited

U.S. PATENT DOCUMENTS

| | | |
|---|---|---|
| 2005/0142249 A1 | 6/2005 | Davis |
| 2014/0249103 A1 | 9/2014 | Buck |
| 2016/0158287 A1 | 6/2016 | Lönnerdal |

FOREIGN PATENT DOCUMENTS

| | | |
|---|---|---|
| CH | 340404 | 8/1959 |
| CN | 102415447 | 4/2012 |

OTHER PUBLICATIONS

Karupaiah and Sundram (Effects of stereospecific positioning of fatty acids in triacylglycerol structures in native and randomized fats: a review of their nutritional implications, Nutrition & Metabolism, Review, Jul. 12, 2007, 4:16) (Year: 2007).*

Zalski et al. (Butyric acid in irritable bowel syndrome, Prz Gastroenterol 2013: 8 (6): 350-353). (Year: 2013).*

Vandenplas et. al. (Human Milk Oligosaccharides: 2-Fucosyllactose (2-FL) and Lacto-N-Neotetraose (LNnT) in Infant Formula, Nutrients 2018, Review, 10, 1161). (Year: 2018).*

Broyard Camille, et al.; "Modifications of structures and functions of caseins: a scientific and technological challenge"; Dairy Science & Technology, vol. 95, No. 6; Mar. 27, 2015; pp. 831-862.

International Search Report and Written Opinion, date of mailing Aug. 17, 2020; International Application No. PCT/EP2020/064498 (16 pgs.).

Souci, et al.; "Food Composition and Nutrition Tables, Dairy Products"; Food Composition and Nutrition Tables, 6th Revised and Completed Edition; Medpharm Scientific Publisher, Stuttgart, Germany; 2000; pp. 1-71.

Huppertz, Thom, et al.; "Salt equilibria in nutritional formulae for infants and young children", International Dairy Journal, vol. 110, Nov. 2020 (7 pgs.).

English translation of First Office Action, Chinese Application No. 202080037839.6 (5 pgs.).

* cited by examiner

*Primary Examiner* — Anand U Desai
*Assistant Examiner* — Jacob A Boeckelman
(74) *Attorney, Agent, or Firm* — Fitch, Even, Tabin & Flannery LLP

(57)    ABSTRACT

The invention relates to a nutritional composition comprising carbohydrates, protein and a fat composition, wherein:
(a) the nutritional composition has a total calcium content on dry matter of at least 3.5 g/kg;
(b) the protein comprises casein;
(c) the nutritional composition has a content of protein-bound calcium of 7.5 mmoles or less per 10 grams of casein; and
(d) the ratio NPN to TN is 0.7 or less, with:
NPN meaning non-protein nitrogen in the nutritional composition in grams per 100 grams of nutritional composition (g/100 g); and
TN meaning total nitrogen (TN) in the nutritional composition in g/100 g.

The invention further relates to a process for the preparation of the nutritional composition in powder form and to the composition for use in the prevention of gut discomfort and constipation in human subjects, in particular human subjects of 0 to 36 months of age.

14 Claims, 5 Drawing Sheets

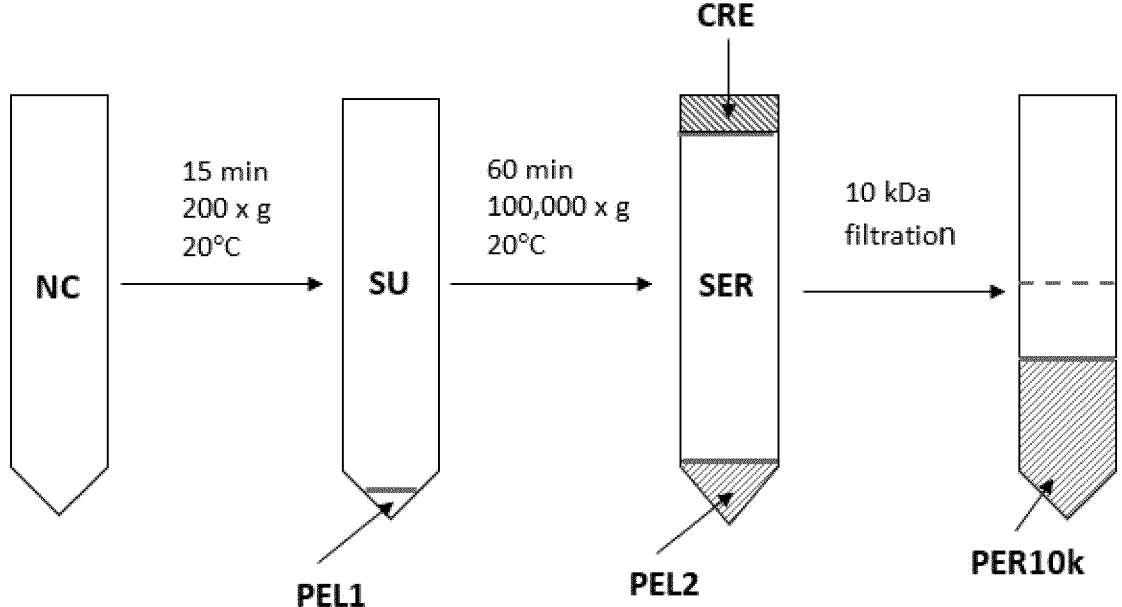
Figure 1   Determining protein-bound calcium

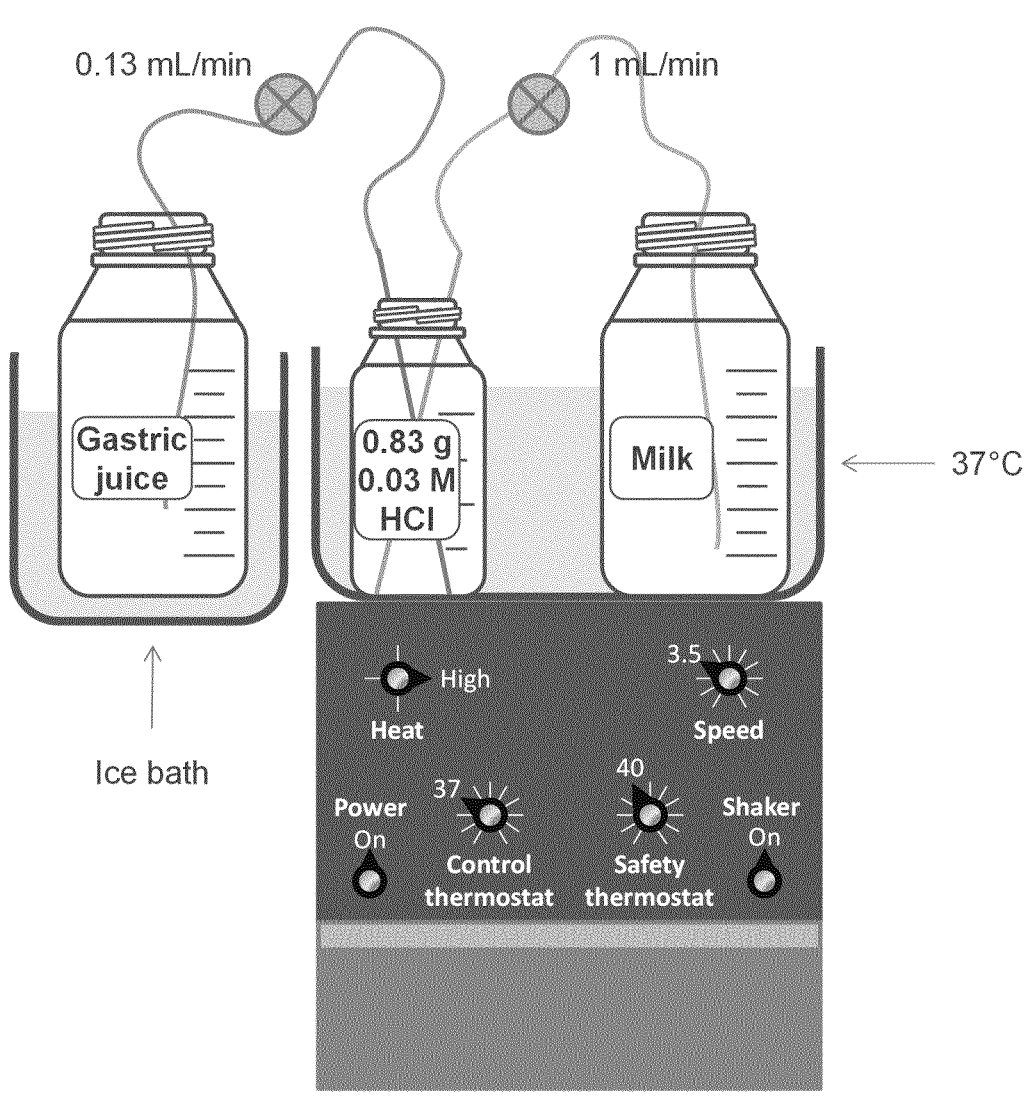
Figure 2  In vitro gastric digestion test set-up

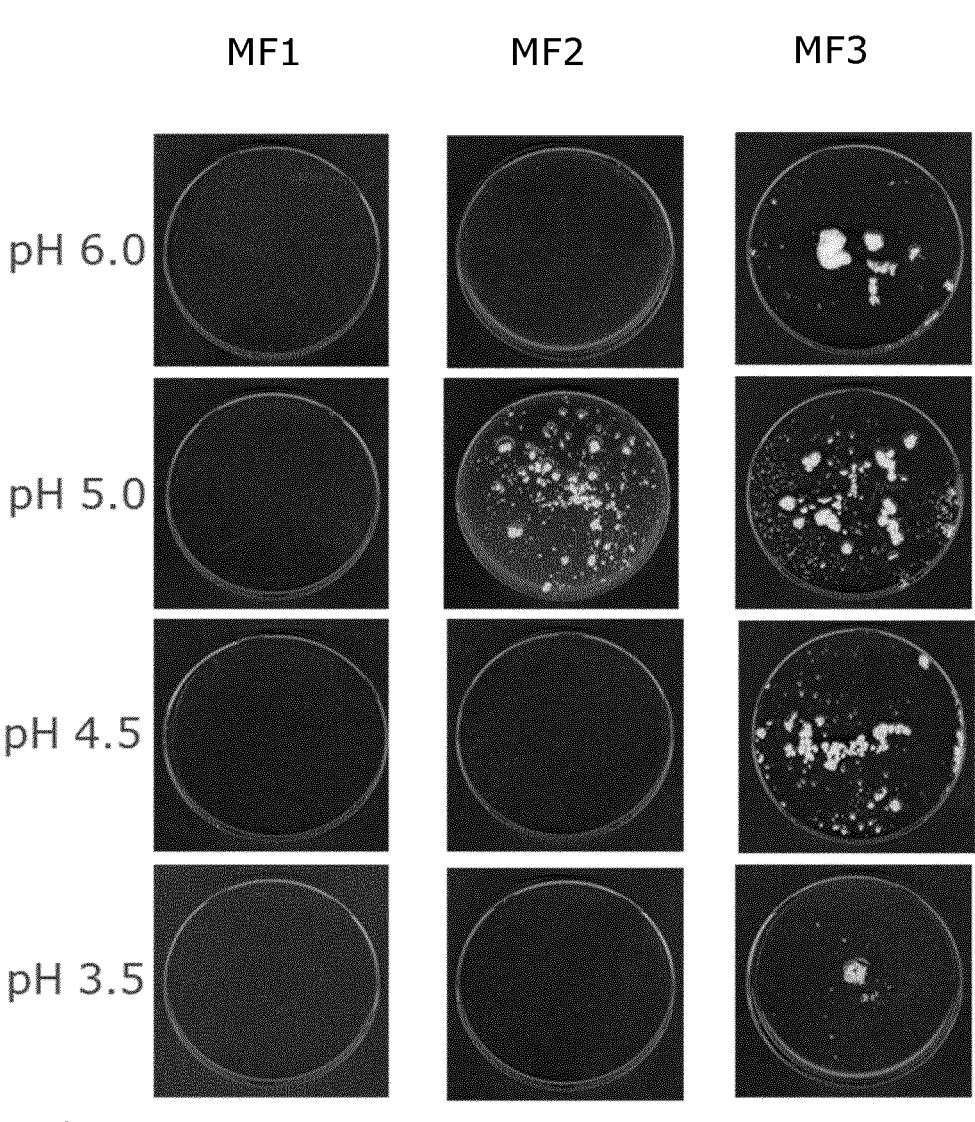
Figure 3  Curd formation

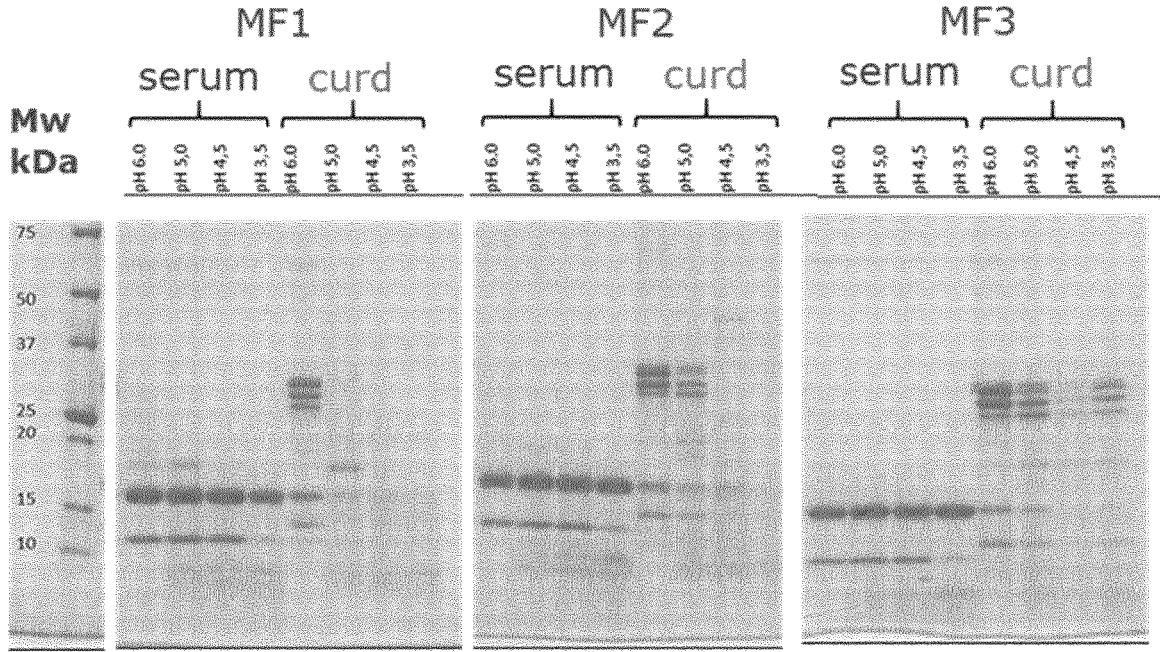
Figure 4  SDS-PAGE electrophoretograms of the model formulations
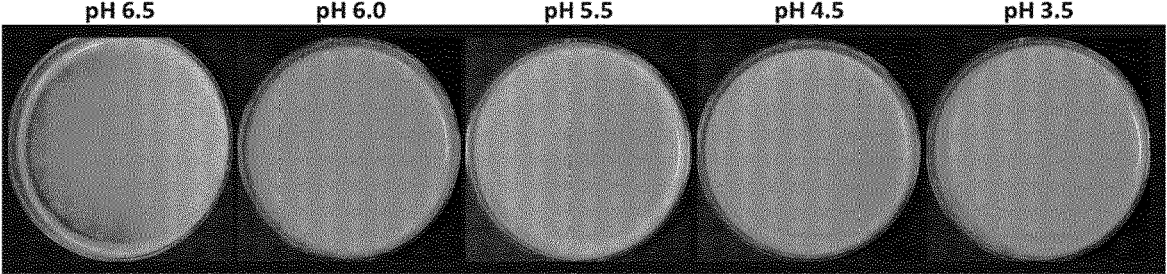
Figure 5  Curd formation

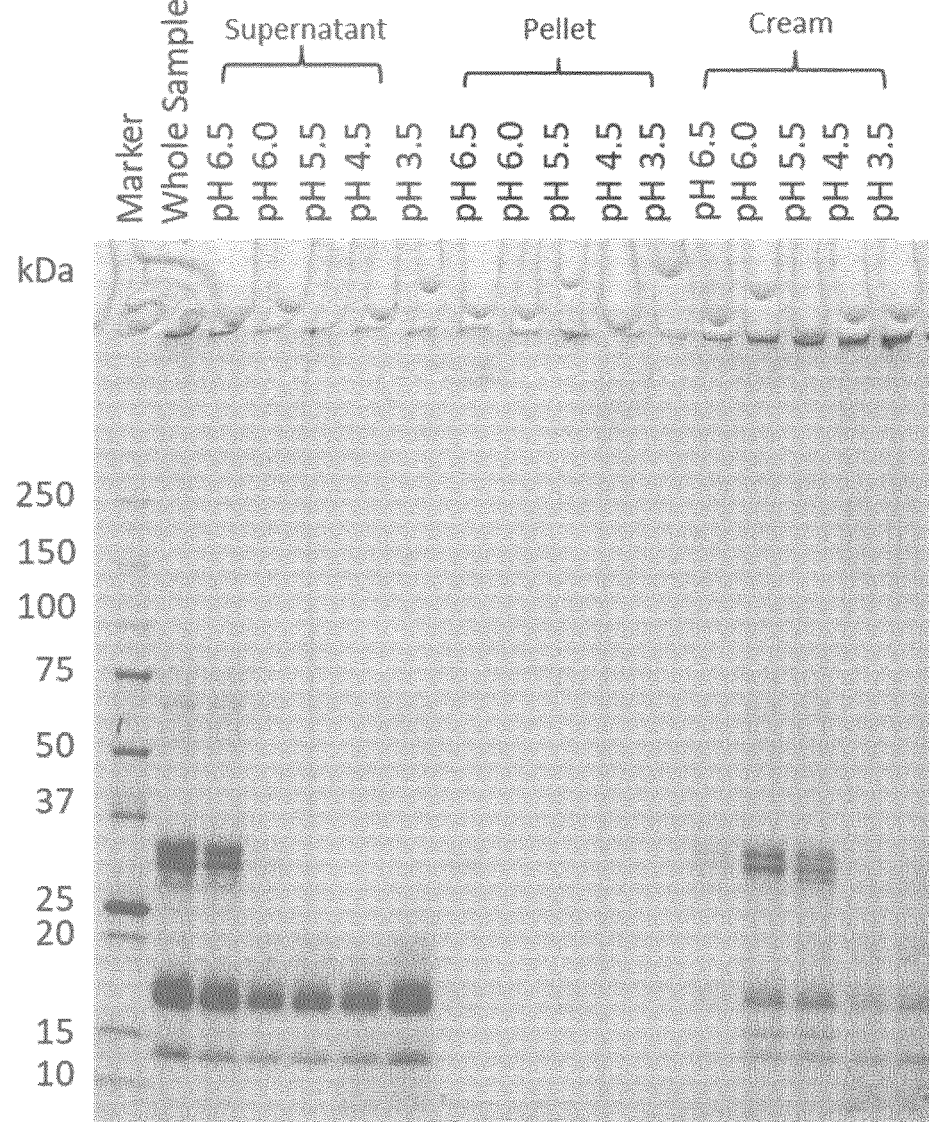
Figure 6    SDS-PAGE electrophoretograms of the nutritional composition of
Example 3

NUTRITIONAL COMPOSITION

CROSS REFERENCE TO RELATED APPLICATIONS

This application is a U.S. national phase application of International Application No. PCT/EP2020/064498, filed May 26, 2020, which claims benefit from European Application No. 19176789.6, filed May 27, 2019, which are each hereby incorporated herein by reference in their entirety.

FIELD OF THE INVENTION

The present invention relates to a nutritional composition, to a process for the preparation of such composition in powdered form and to particular uses of the nutritional composition.

BACKGROUND TO THE INVENTION

It has been considered for a long time by nutritionists that the best food or nutrition supplied to an infant up to the age of at least 6 months is its own mother's milk; i.e. fresh human milk. It is recognized, however, that many situations arise wherein the infant cannot be fed mother's milk and as a result cows' milk based formulas have been prepared and used to nourish an infant. These formulas contain a mixture of casein and whey proteins to provide an amino acid profile as close as possible to that of mother's milk. Much effort has been made to improve infant milk formulas to more closely mimic mother's milk. Also older children above the age of 6 months are fed formulations for weaning purposes in the form of follow-on formulas and growing-up milk formulas. It is important that infant formulas as well as follow-on formulas and growing-up milk formulas show desirable gastric digestion properties.

The protein systems of human milk and cows' milk differ substantially, both quantitatively and qualitatively. Prominent quantitative differences include a lower total protein content, often expressed as the total nitrogen content multiplied by 6.25 or 6.38, of human milk (11 g/L) compared to cows' milk (33-35 g/L). Total nitrogen containing components in milk can be divided into true protein nitrogen and non-protein nitrogen (NPN), with caseins and serum proteins (the latter also called whey proteins) as the main classes of proteins. Caseins are the proteins from milk that precipitate at pH 4.6, whereas whey proteins remain soluble at this pH. In mature human milk, the ratio of whey protein to casein is typically about 60:40 to 50:50, whereas the whey protein to casein ratio is approximately 18:82 in cows' milk.

Although infant formulas have become better and better over time, there are still important differences between human milk and cows' milk based infant formulas that may lead to infants who are fed with such infant formula to suffer from gut discomfort and/or even constipation caused by a poorer gastric digestion. This may lead to babies crying more and hence to more anxiety with parents. By contrast, breast-fed infants exhibit frequent and looser/watery stools which, in return, leads to a better gut comfort.

An important cause for gut discomfort when using infant formula is the formation of curd in the stomach during gastric digestion. Such curd is formed by casein micelles clogging together. If too much of such solid curd is formed, emptying of the stomach becomes more difficult and a feeling of gut discomfort or even constipation may be the result.

The present invention aims to provide a nutritional composition which exhibits improved gastric digestion properties by avoiding, or anyhow significantly reducing, curd formation in the stomach during the gastric digestion process, thereby facilitating stomach emptying and improving gut comfort.

SUMMARY OF THE INVENTION

It was found that by carefully controlling the amount of calcium in a nutritional composition, in particular the amount of protein-bound calcium, curd formation in the stomach can be significantly reduced or even avoided, thereby improving gastric digestion. Accordingly, the present invention relates to a nutritional composition wherein the protein component comprises casein micelles having a protein-bound calcium content of 7.5 mmoles or less per 10 grams of casein and total calcium content is at least 3.5 g/kg with the ratio of non-protein nitrogen (NPN) to total nitrogen (TN) being 0.7 or less.

The invention further relates to a process for the preparation of such nutritional composition in powdered form, wherein at certain moments during the preparation salts (sometimes also referred to as minerals) are added which comprise (i) a calcium-binding acid or water-soluble salt thereof and (ii) at least one calcium salt selected from calcium citrate, calcium phosphate and calcium carbonate.

DETAILED DESCRIPTION OF THE INVENTION

In a first aspect the present invention relates to a nutritional composition comprising carbohydrates, protein and a fat composition, wherein:

(a) the nutritional composition has a total calcium content on dry matter of at least 3.5 g/kg;

(b) the protein comprises casein;

(c) the nutritional composition has a content of protein-bound calcium of 7.5 mmoles or less, preferably between 3 and 6 mmoles, per 10 grams of casein; and (d) the ratio NPN to TN is 0.7 or less, preferably between 0.01 and 0.5, more preferably between 0.03 and 0.3, most preferably between 0.05 and 0.15, with:

NPN meaning non-protein nitrogen in the nutritional composition in grams per 100 grams of nutritional composition (g/100 g); and TN meaning total nitrogen (TN) in the nutritional composition in g/100 g.

Calcium is an important element that needs to be present in the nutritional composition. Minimum levels are prescribed by the relevant regulations. Calcium could come from various sources, such as from any milk-based ingredient, notably skimmed milk, whole milk and/or cream, or from one or more calcium salts that are added separately. For the purpose of the present invention it is important that the total calcium content on dry matter in the nutritional composition is at least 3.5 grams of Ca per kilogram (g/kg). Preferably, total calcium content is in the range from 3.5 to 9.5, more preferably 3.6 to 8.0 g/kg on dry matter. Calcium content can be determined using Inductively Coupled Plasma Mass Spectrometry (ICP-MS) as described in standard method ISO 21424:2018 (IDF 243)—*Milk, milk products, infant formula and adult nutritionals—Determination of minerals and trace elements—Inductively coupled plasma mass spectrometry (ICP-MS) method.*

The calcium in the nutritional composition can essentially come from two sources. Firstly, calcium could come from the dairy ingredients used as starting materials for the nutritional composition. Such dairy ingredients could, for example, include cream, skimmed milk, whole milk and/or a whey ingredient such as native whey, demineralized whey or a combination of both. Secondly, calcium could also originate from calcium salts that are added. Such calcium salts should be salts that are allowable for use in food products and in particular in nutritional compositions for infants and young children. Examples of suitable calcium salts are calcium citrate, calcium phosphate and calcium carbonate. Using a combination of two or more of such calcium sources is also possible. As will be appreciated by those skilled in the art calcium phosphate salts can appear in different forms. For the purpose of the present invention the calcium phosphate salt can be in various forms, provided that in each case one mole of the salt contains at least one mole of calcium and one mole of orthophosphate. Suitable examples include calcium hydrogen phosphate, calcium dihydrogen phosphate, calcium phosphate, dicalcium disphosphate, calcium triphosphate and tricalcium phosphate.

The nutritional composition of the present invention comprises a protein component. It was found to be critical that the calcium bound to the proteins present is carefully controlled and should not exceed a certain value in order to minimize or even completely avoid curd formation in the stomach. As indicated above cows' milk proteins can be divided into caseins and serum proteins (also called whey proteins). The ratio of whey protein to casein in cows' milk is approximately 18:82. Under neutral conditions the vast majority of caseins will be present as micelles. In cows' milk the calcium can be present as (dissolved) salt and as protein-bound calcium. The majority of the protein-bound calcium (more than 90 wt %, typically more than 95 wt %) will be bound into the caseins and casein micelles with the remainder up to 100% being associated with whey proteins. It was found that particularly this protein-bound calcium plays an important role in the curd formation in the stomach. Accordingly, in the nutritional composition of the invention the content of such protein-bound calcium should be 7.5 mmoles or less, preferably between 3 and 6 mmoles, per 10 grams of casein.

In general, the amount of protein-bound calcium in a nutritional composition is determined as follows. Referring to FIG. 1 for a schematic representation of the procedure, the liquid nutritional composition NC (if in powder form, the nutritional composition is first reconstituted in water) is first equilibrated at 20° C. for 1 hour and centrifuged at 200×g for 15 minutes at 20° C. to remove insoluble calcium salts, followed by separation of the pellet (PEL1) and supernatant (SUP). The SUP is subsequently equilibrated at 20° C. for 2 hours prior to centrifugation at 100,000×g for 60 minutes at 20° C. The resulting liquid serum layer (SER) is separated from the cream layer (CRE) and pellet (PEL2) and subsequently filtered through a 10 kDa membrane to obtain the 10 kDa-permeable fraction of the sample (permeate, PER10kD). Total calcium (<Ca>) concentration in grams per kilogram (g/kg) in the SUP and the PER10kD is determined by the ICP-MS method described above. The concentration of protein-bound calcium (PBCa, in g/kg) is then determined as the fraction of calcium in milk that does not permeate through the 10 kDa membrane:

$$PBCa = \ <Ca> \ \text{in } SUP\text{-} \ <Ca> \ \text{in } PER10kD$$

4

Casein nitrogen content (CN) in a milk based liquid (in g/100 g product) is determined as described in ISO17997/ IDF 29-1—*Determination of casein nitrogen content—Part 1—Indirect method (Reference method)*. Casein content in the milk-based liquid (Cas) in g/100 g then is:

$$Cas = CN \text{ in milk-based liquid} * 6.38$$

Casein content (Cas) in nutritional compositions can also be determined differently, particularly if the processing history of the composition is unknown and whey protein denaturation may have occurred during such processing. In such a case, some of the whey protein will be determined as CN in aforesaid method ISO17997/IDF 29-1 and, as a result, inaccurate values for CN will arise and the resulting casein content will not be correct. When using the more elaborate method described below, however, one would always find the correct casein content. Accordingly, in this more elaborate method for determining casein content of a nutritional composition total nitrogen content (TN), non-protein nitrogen (NPN) and amino acid composition of the composition are determined first. TN is determined using the Kjeldahl method as described in method ISO 8968-1/IDF 020-1 (*Milk and milk products—Determination of Nitrogen Content— Part 1: Kjeldahl Principle and Crude Protein Calculation*). NPN is determined as described in method ISO 8968-4/IDF 020-4 (*Milk and milk products—Determination of Nitrogen Content—Part 4: Determination of non-protein-nitrogen content*). Both TN and NPN are expressed in grams per 100 grams of nutritional composition (g/100 g). Amino acid composition is determined by ion exchange chromatography based on methods described in AOAC Official Method 994.12—*Amino Acids in Feeds*. From the concentrations of the amino acids proline (Pro), phenylalanine (Phe), aspartic acid plus asparagine (Asp+Asn) and alanine (Ala) the ratio of whey proteins to casein in the nutritional composition is subsequently calculated as described in AOAC Official Method 2012.7—*Calculation of Whey Protein Fraction in Milk-Based Infant Formula*. Based on TN and NPN total protein content can be calculated as (TN-NPN)*6.38. Based on total protein content and the ratio of whey proteins to casein, casein content in the nutritional composition (in g/100 g) can subsequently be determined.

The amount of protein-bound calcium (i.e. the ratio PBCa/Cas) is then calculated as amount of protein-bound calcium in mmoles per 10 grams of casein by using the formula:

$$PBCa/Cas = \frac{1000 * [PBCa/MW(Ca)]}{Cas}$$

with MW(Ca) being the mole weight of calcium in g/mole (=40 g/mole), PBCa being the protein-bound calcium in g/kg and Cas being the amount of casein in g/100 g (which is equivalent to an amount*10 g/kg). The amount of protein-bound calcium is determined at standard pH of about 7 (i.e between 6.5 and 7.5).

In order to ensure that the amount of protein-bound calcium is below the 7.5 mmoles/10 g casein-threshold, specific measures in the preparation of the nutritional composition may be needed. However, it could also be that certain cow breeds produce milk having a protein-bound calcium content in the desired range. If, on the other hand, specific measures are needed, this will typically involve the use of one or more calcium-binding substances that are allowable to be used in food products and specifically in infant formula, follow on formula and growing up milk formula. Accordingly, calcium-binding acids or water-soluble salts thereof that can be used in food products can be used. Suitable examples are citric acid and citrate salts. Since potassium and sodium are usually also added as salts, the use potassium and/or sodium citrate as calcium binding substances is preferred. The amount of calcium-binding substance(s) to be used will depend on the protein-bound calcium level in the milk which is used as the starting material. In addition to or instead of the addition of calcium-binding substances, measures to bring the protein-bound calcium to the right level could also involve adding casein-ates as low calcium casein source or processing of the starting milk to reduce the amount of protein-bound calcium. Such processing could involve membrane filtration under specific conditions, treating the starting milk with an ion exchange resin and/or subjecting the milk to a electro-dialysis treatment.

The ratio of NPN to TN in the nutritional composition should be 0.7 or less and preferably ranges between 0.01 and 0.5, more preferably between 0.03 and 0.3 and most preferably between 0.05 and 0.15. Generally, a high ratio of NPN/TN in nutritional compositions (i.e. above 0.7) is indicative of the use of extensively hydrolyzed proteins in these products. A key aspect of the present invention is that a large proportion of the proteins present in the nutritional composition have their native form and hence are in a non-hydrolyzed state.

Total nitrogen, TN, is determined using the Kjeldahl method as described in method ISO 8968-1/IDF 020-1 (*Milk and milk products—Determination of Nitrogen Content—Part* 1: *Kjeldahl Principle and Crude Protein Calculation*). In addition, non-protein nitrogen content, NPN, for the reconstituted samples is determined as described in method ISO 8968-4/IDF 020-4 (*Milk and milk products—Determination of Nitrogen Content—Part* 4: *Determination of non-protein-nitrogen content*). Both TN and NPN are expressed in grams per 100 grams of nutritional composition (g/100 g).

The fat composition used in the nutritional composition could in principle be any fat composition known for use in infant formula and formula for young children. Such fat composition could consist of two or more components added at different stages in the preparation process. It is, however, preferred that at least part of the total fat composition used originates from bovine milk fat. More specifically, it is preferred that the fat composition comprises at least 20% by weight, preferably at least 45% by weight, based on total weight of the fat composition of triacylglycerols (TAG) originating from a bovine milk fat source. Preferred bovine milk fat sources are whole milk, cream and anhydrous milk fat. Any one of these bovine milk fat sources could be used as well as any combination of two or more of these bovine milk fat sources.

In a particularly preferred embodiment the fat composition used in the nutritional composition of the present invention comprises (a) 0.5-2.2% by weight, preferably 0.6-2.0% by weight, based on total weight of fatty acid acyl groups in TAG of butanoate groups (C4:0); and (b) 18.0-35.0% by weight, preferably 19.0 to 32.0% by weight, based on total weight of fatty acid acyl groups in TAG of long chain saturated fatty acid acyl groups having a chain length of 12 or more carbon atoms at the sn-1 and sn-3 position in TAG.

The content of the different fatty acids in the fat composition can be determined by standard method ISO 15884/IDF 182:2002 (*Milk fat—Preparation of fatty acid methyl esters*) and ISO 15885/IDF 184 (*Milk fat—Determination of the fatty acid composition by gas-liquid chromatography*). The distribution of fatty acids over the glycerol backbone can be determined according to the method disclosed in Luddy, F. E., Barford, R. A., Herb, S. F., Magidman, P. and Riemenschneider, R. W. J. *Am. Oil Chem. Soc.*, 41, 693-696 (1964). In essence, this method involves hydrolysis of TAG by a sn-1,3 specific pancreatic lipase (porcine). The required 2-monoacylglycerols formed are isolated by thin layer chromatography and these are subsequently methylated for gas chromatographic analysis and quantified in molar concentrations. The molar concentration of a fatty acid at the sn-1,3 positions of the glycerol backbone [FA(sn-1,3)] is calculated from the molar concentration of this fatty acid in the total fat [FA-TAG] and the molar concentration of this fatty acid at the sn-2 position [FA(sn-2)] via the formula:

$$[FA(sn\ 1,3)] = [FA(TAG)] - \frac{1}{3} * [FA(sn2)]$$

The nutritional composition of the invention also comprises carbohydrates. Typically such carbohydrates will largely consist of lactose. Other carbohydrate ingredients, such as oligosaccharides (for example, fructo-oligosaccharides and/or galacto-oligosaccharides), may be included as well. In a particularly preferred embodiment the nutritional composition of the invention also comprises at least one human milk oligosaccharide. Suitable human milk oligosaccharides include fucosylated lactoses, in particular 2'-fucosyllactose (2'-FL) and 3-fucosyllactose (3-FL), lacto-N-tetraose (LNT), lacto-N-neotetraose (LNnT) and 6'-siallyllactose (6'-SL). Of these, 2'-FL is most preferred. If present, the total amount of human milk oligosaccharide on dry matter in the nutritional composition is suitably 0.05 to 2.0 grams, more suitably 0.1 to 1.0 grams, per 100 grams (g/100 g).

The nutritional composition is particularly suitable for human subjects of 0 to 36 months of age, in particular infants (a person of 0-12 months of age according to the CODEX Alimentarius (CODEX STAN 72-1981), further referred to as the CODEX) and young children up to the age of 36 months. Nutritional compositions for infants are commonly referred to as infant formula, for older children the terms follow on formula and growing up milk, as described hereinbefore, are also commonly used. When used as infant formula, the nutritional composition according to the present invention should contain the ingredients in the amounts as prescribed by the CODEX and, if needed, as prescribed by additional regulations of individual countries. Accordingly, the nutritional composition according to the invention for infants comprises the protein, carbohydrates and fat composition as described above, and will also comprise vitamins, salts and trace elements and the other substances in accordance with the specifications prescribed by the CODEX and, if needed, by additional national regulations.

The nutritional composition of the invention can be in the form of ready-to-feed formulation, either in drinkable or spoonable form, or in the form of a powdered formula. In the form as produced, transported and sold, it is suitably in powder form. The powder can subsequently be mixed with water to obtain the ready-to-drink or ready-to-spoon formula as consumed by the infant or young child. The pH of the final nutritional composition in its ready-to-drink or ready-to-spoon form would typically be between 6.5 and 7.5, which is the standard pH for this type of food product.

The present invention also relates to a process for the preparation of a nutritional composition in powder form as described above, which process comprises the steps of (a) preparing a mixture comprising a whey protein source, a casein source, a fat source, a carbohydrate source and salts;

(b) spray drying the mixture resulting from step (a) into a powder; and (c) optionally dry-blending salts into the powder resulting from step (b) to obtain the nutritional composition, wherein the salts comprise (i) a calcium-binding acid or water-soluble salt thereof; and (ii) at least one calcium salt selected from calcium phosphate and calcium carbonate, and wherein the calcium-binding acid or water-soluble salt thereof is added in step (a) and the at least one calcium salt is added in step (a) and/or in step (c).

Step (a) of the process can be carried out by any way known in the art. Each of the components of the mixture, i.e. the whey protein source, the casein source, the fat source, the carbohydrate source and the salts, may itself consist of two or more sub-components or may be combined with one or more of the other components into a single ingredient. For example, the fat source could consist of one or more bovine milk fat components and one or more vegetable fats and/or oils components, each of which could be added at different stages during step (a). On the other hand, if used, whole milk would be used as fat source, whey protein source, casein source, carbohydrate source and source of salts, all combined in a single ingredient. Likewise, skimmed milk would be a combined whey protein source, casein source, carbohydrate source and source of salts. The salts could also comprise multiple different salt components, which could be added during step (a), but possibly also during dry-blending step (c). For the purpose of the process of the invention the salts should anyhow comprise (i) a calcium-binding acid or water-soluble salt thereof; and (ii) at least one calcium salt selected from calcium citrate, calcium phosphate and calcium carbonate with calcium phosphate and calcium carbonate being preferred. For the purpose of the present invention it is even more preferred to use a combination of both these calcium salts, as it enables a more accurate finetuning of protein-bound calcium levels in the final nutritional composition.

The calcium-binding acid or water-soluble salt thereof is suitably selected from citric acid, sodium citrate, potassium citrate and any combination of two or more of these, preferably a combination of sodium citrate and potassium citrate.

The whey protein source used could in principle be any whey protein source conventionally used or useful in the preparation of nutritional compositions. For the purpose of the present invention demineralized whey is suitably used. However, a whey product isolated from raw milk with a minimum of heat treatments to retain as much of the whey proteins in their native state (so called native whey), could also be used.

The different ingredients can be added at different stages during step (a). For example, step (a) could be carried out by the successive steps of:

(a1) blending the combined casein source(s), the milk fat source(s) and the whey protein source(s);

(a2) heating the resulting mixture to evaporate part of the water included in such mixture followed by cooling the mixture;

(a3) adding salts and vitamins to the cooled mixture;

(a4) pasteurization; and (a5) adding a vegetable oil source, typically one or more vegetable oil blends, and homogenizing the mixture.

The resulting homogenized mixture can subsequently be spray dried in step (b). The casein source and milk fat source used in step (a1) could be two distinct components, such as skimmed milk (casein source) and cream or anhydrous milk fat (milk fat source), but could also be combined into as single component, such as whole milk.

As is well known evaporation, pasteurization and homogenization, if needed, can be carried out at different moments in different orders during step (a). The example given above is just one way of blending all ingredients together. In principle, any order of steps resulting in a uniform mixture of all ingredients could be used.

In step (b) the mixture resulting from step (a) is spray-dried to obtain the nutritional composition in powder form. Spray-drying is a well-known technique and any spray drying technique suitable for producing a powder from the liquid nutritional composition mixture resulting from step (a) could be used.

In optional step (c), finally, further ingredients can be dry-blended into the powder resulting from step (b) to obtain the final nutritional composition powder. One ingredient that could be dry-blended in this step (c) is (part of) the salts, in particular calcium citrate, calcium phosphate and/or calcium carbonate. In the process of the invention the calcium-binding acid or water-soluble salt thereof is added in step (a) whilst the calcium salt(s) is(are) added in step (a) and/or in step (c). The calcium-binding component is suitably added before the addition of the calcium salt(s). In addition to salts other ingredients could also be added during dry-blending step (c). Such ingredients include, for example, vitamins, lactose, galacto-oligosaccharides (GOS), human milk oligo-saccharides (HMOs) and (premixes of) trace elements that are suitably present in nutritional compositions. This is well known in the art.

The nutritional composition of the invention was found to lead to less curd formation in the stomach—or even no curd formation at all-, thereby facilitating stomach emptying and gastric digestion. This helps to prevent gut discomfort and constipation in infants and little children. Accordingly, in a further aspect the present invention relates to the nutritional composition as described above for use in the prevention of gut discomfort and constipation in human subjects, suitably human subjects of 0 to 36 months of age.

The invention is further illustrated by the following examples without, however, limiting the scope of the invention to these particular embodiments.

DESCRIPTION OF FIGURES

FIG. 1 is a schematic representation of the procedure for determining protein-bound calcium.

FIG. 2 shows the set-up of the in vitro gastric digestion model used.

FIG. 3 shows photographic images after in-vitro gastric digestion of two samples according to the invention and one comparative sample at different pH values.

FIG. 4 shows SDS-PAGE electrophoretograms of the model formulations tested.

FIG. 5 shows photographic images after in-vitro gastric digestion of a nutritional composition according to the invention.

FIG. 6 shows SDS-PAGE electrophoretograms of the nutritional composition of Example 3.

EXAMPLES

Example 1—Preparation of Model Formulations

Model formulations with different levels of protein-bound calcium were prepared and tested in vitro to demonstrate the effect of protein-bound calcium on curd formation in the stomach during gastric digestion.

Milk samples with differing degrees of casein mineralization were prepared using the method described by Pyne & McGann (Pyne, G. T., & McGann, T. C. A. (1960). *The colloidal phosphate of milk: II. Influence of citrate. Journal of Dairy Research,* 27(1), 9-17).

For this purpose, a batch of 50 kg of pasteurized skim milk was obtained. Three subsamples (200 g each) were taken, one of which (Sample 2) was kept at its original pH, whereas Sample 1 was adjusted to pH 5.7 by the addition of 1 M hydrochloric acid (acid) and Sample 3 was adjusted to pH 8.0 by the addition of 1 M sodium hydroxide (base). The pH adjustment was carried out at 5° C., with milk samples as well as acid and base equilibrated at this temperature for 1 hour prior to pH adjustment.

Due to the pH adjustment the salt balance in the milk had changed. In order to re-equilibrate the serum composition of the adjusted milk the samples are dialyzed. Accordingly, Samples 1, 2 and 3 were subsequently exhaustively dialyzed against the original pasteurized skim milk using a dialysis membrane with a nominal molecular weight cut-off of 14 kDa. The first dialysis was carried out for 24 h at 5° C. whereby for each of Samples 1, 2 and 3 200 g milk was dialyzed against 5000 g of the original pasteurized milk with gentle agitation. Following this dialysis stage, the dialysis tubes were transferred to another container containing 5000 g of the original pasteurized skim milk at 5° C. and dialysis was again conducted under the same conditions for 24 h. Following this dialysis step, samples were removed from the dialysis tubing.

The pH of the dialyzed Samples 1DIA (dialyzed sample obtained from Sample 1), 2DIA (dialyzed sample obtained from Sample 2) and 3DIA (dialyzed sample obtained from Sample 3) was 6.8 as measured at 20° C. using standard equipment.

Samples 1DIA, 2DIA and 3DIA were subsequently used to prepare Model Formulations MF1, MF2 and MF3, respectively, by mixing 21 g of the respective dialyzed sample with 21 g of demineralized whey (DEMINAL® 90 Liquid ex FrieslandCampina Ingredients, having total protein content on dry matter of 13.5 wt %, lactose content on dry matter of 84.5 wt %, calcium content on dry matter of 0.040 wt % and total solids content of 28 wt %) and 58 g of milk permeate produced by ultrafiltration of pasteurized skimmed milk at 50° C. using a 10 kDa membrane and having TN of less than 0.05 g/100 g, a lactose content of 4.9 wt %, and calcium content 0.028 wt %.

Model formulations MF1, MF2 and MF3 were subsequently analyzed for total nitrogen content (TN), non-protein nitrogen content (NPN), casein nitrogen content (CN) and calcium content (Ca). The ratio protein-bound calcium to casein (PBCa/Cas) was subsequently calculated in mmoles Ca per 10 g casein.

TN was determined using the Kjeldahl method as described in method ISO 8968-1/IDF 020-1 (*Milk and milk products—Determination of Nitrogen Content—Part* 1: *Kjeldahl Principle and Crude Protein Calculation*).

NPN was determined as described in method ISO 8968-4/IDF 020-4 (*Milk and milk products—Determination of Nitrogen Content—Part* 4: *Determination of non-protein-nitrogen content*).

CN was determined as described in ISO17997/IDF 29-1—*Determination of casein nitrogen content—Part* 1—*Indirect method* (*Reference method*). Casein content of the dialyzed sample is then calculated as CN*6.38.

Calcium content was determined using Inductively Coupled Plasma Atomic Mass Spectrometry (ICP-MS) as described in standard method ISO 21424 I IDF 243:2018 (*Milk, milk products, infant formula and adult nutritionals—Determination of minerals and trace elements—Inductively coupled plasma atomic mass spectrometry* (*ICP-MS*) *method*).

PBCa was determined as described hereinbefore with reference to FIG. 1. Accordingly, samples of MF1, MF2 and MF3 were first equilibrated at 20° C. for 1 hour and centrifuged at 200×g for 15 minutes at 20° C. to remove any insoluble calcium salts, followed by separation of the pellet and supernatant (SUP). The SUP is subsequently equilibrated at 20° C. for 2 hours prior to centrifugation at 100,000×g for 60 minutes at 20° C. The resulting liquid serum layer is separated from the cream layer and pellet and subsequently filtered through a 10 kDa membrane to obtain the 10 kDa-permeable fraction of the sample (PER10 kD). Total calcium (<Ca>) concentration in grams per kilogram (g/kg) in the SUP and the PER10kD was determined by the ICP-MS method described above. The concentration of protein-bound calcium (PBca, in g/kg) was calculated as:

PBCa=<Ca> in SUP−<Ca> in PER10 kD

Key parameters of model formulations MF1, MF2 and MF3 are indicated in Table 1.

TABLE 1

| Compositional parameters of model formulations MF1, MF2 and MF3 | | | |
|---|---|---|---|
| | Sample MF1 | Sample MF2 | Sample MF3 |
| Ca (g/kg) | 0.40 | 0.45 | 0.47 |
| NPN (g/100 g) | 0.03 | 0.03 | 0.03 |
| TN (g/100 g) | 0.25 | 0.26 | 0.25 |
| CN (g/100 g) | 0.09 | 0.09 | 0.09 |
| NPN/TN | 0.12 | 0.12 | 0.12 |
| CN/TN | 0.4 | 0.4 | 0.4 |
| PBCa/Cas (mmol/10 g casein) | 5.4 | 7.1 | 8.0 |

Example 2—In Vitro Gastric Digestion

In-vitro gastric digestion of formulations MF1, MF2 (both according to the invention) and MF3 (comparative) was conducted using a semi-dynamic digestion model at NIZO (Ede, The Netherlands) with digestive conditions adapted to mimic infant gastric conditions.

For the in-vitro gastric digestion the samples, a system as outlined in FIG. 2 was used. For typical experiments, 0.83 g 30 mM HCl was placed in a 100 mL bottle placed in an agitating waterbath set at 37° C. and ~120 rpm. The sample was also equilibrated at 37° C. 20 mL of the sample was subsequently fed into the bottle at a rate of 1 mL/min, whereas gastric juice (30 mM HCl containing 250 U/mL pepsin and 8.75 U/mL lipase) was added at a rate of 0.13 mL/min. Gastric juice was kept on ice to prevent losses in enzyme activity. Porcine pepsin (Sigma) was used as the pepsin source in the gastric juice, whereas Amano lipase A (Amano) was the standard lipase used.

Standard conditions for the in-vitro gastric digestion are summarized in Table 2.

TABLE 2

| Standard conditions for in-vitro gastric digestion | |
| --- | --- |
| Gastric Juice | 30 mM HCl |
| | 8.75 U/mL lipase A |
| | 250 U/mL pepsin |
| Production rate | 0.4 mL/min |
| Enzymes | Amano lipase A from Aspergullus niger |
| | Pepsin from porcine gastric mucosa |
| Fasting gastric pH | 3.5 |
| Product feeding rate | 1.0 mL/min |
| Feeding time | 20 min |
| Amount of product | 20 mL |

To allow sampling at specified pH values, buffering curves of samples were first determined. For this purpose, samples were mixed with different volumes of 30 mM HCl and the pH was determined. Based on the amount of 30 mM HCl required to reach a certain pH and the pumping speed, the time point at which the sample should be taken could be calculated. To inhibit pepsin activity after sampling, a pepstatin A stock solution (0.02 g Pepstatin A in 18 mL methanol+2 mL glacial acetic acid) was added at a level of 50 μL/10 mL of digested sample.

At set points during the digestion (pH 6.0, 5.0, 4.5, 3.5) a product was removed (a separate product was used for each pH point) and the contents of the container were poured into a petri-dish and photographed, for visual observation of curd formation and breakdown. Subsequently, samples were centrifuged at 4000×g for 10 min and pellet and supernatant were separated by decanting. Both fractions were weighed and freeze-dried and subsequently analyzed by SDS-PAGE under reducing conditions.

FIG. 3 shows photographic images of the model formulations after the in-vitro gastric digestion at different pH values. Diameter of the container in which the samples were photographed was 88 mm. FIG. 3 shows that visible curd formation was not observed in Sample MF1 (according to the invention) at any pH. In Sample MF2 (according to the invention), visible coagulation was not observed at pH 6.0, but as digestion progressed coagulation was observed at pH 5.0. Upon further progression, however no residual curd particles were observed in this sample, indicating the breakdown of curd particles formed initially. For Sample MF3 (comparative), strong coagulation was already observed at pH 6.0 and although some breakdown of particles was observed over time, even at the end of digestion (pH 3.5; >120 min) large residual curd particles were still observed.

The samples MF1, MF2 and MF3 were also centrifuged, yielding a pellet and a supernatant (serum), and analyzed by SDS-PAGE under reducing conditions. As outlined in FIG. 4, intact caseins, observed on SDS-PAGE gels in the range 25-35 kDa, were only observed in the original samples and in the pellets formed.

Residual intact caseins were observed in the pellet of all samples MF1, MF2 and MF3 at pH 6.0; however, at pH 5.0, no residual intact casein was observed anymore in sample MF1, whereas samples MF2 and MF3 still showed residual intact casein. At lower pH the intact casein is no longer observed in sample MF2. In sample MF3, however, even at the end of the digestion process (pH 3.5) residual intact casein was still observed, probably contained within the large curd particles still observed in these samples as well (see FIG. 3). Hence, it is apparent that the size of the curd particles formed is a key factor determining the rate of casein breakdown in the samples. If large particles are formed, the total particle surface area is lower and with diffusion of digestive enzymes through the particles likely a rate-limiting step, casein breakdown is slow.

Example 3—Nutritional Composition

A composite blend was prepared from thermised whole milk, cream and demineralized whey. To that effect 145 kg of the whole milk was blended with 163 kg of the demineralized whey and 16 kg of the cream. TN, NPN, total calcium content and casein content of each ingredient and of the composite blend were determined as described above. In addition, and protein-bound calcium (PBCa) of the milk and the composite blend was determined as described above. Fat content was determined using the Rose Gottlieb method (ISO 1211/IDF 1, Milk—Determination of fat content—*Gravimetric method* (*Reference method*). The results are indicated in Table 3.

TABLE 3

| | Properties | | | | | |
| --- | --- | --- | --- | --- | --- | --- |
| Sample | TN (g/100 g) | NPN (g/100 g) | NPN/ TN | Fat (g/100 g) | Ca (g/kg) | PBCa/ Cas (mmol/ 10 g) |
| Milk | 0.54 | 0.03 | 0.06 | 4.3 | 1.20 | 7.3 |
| Cream | 0.33 | 0.02 | 0.06 | 42.2 | 0.61 | — |
| Whey | 0.56 | 0.06 | 0.11 | 0.2 | 0.056 | — |
| Blend | 0.54 | 0.05 | 0.09 | 4.1 | 0.60 | 6.3 |

The composite blend was subjected to an evaporation treatment and further ingredients were added (see Table 4 for recipe). The resulting mixture was pasteurized, homogenized and spray-dried, yielding a spray-dried base powder with a moisture content of 2.5%. To the spray-dried base powder, further ingredients were added by dry blending, which are shown in Table 4.

The final nutritional composition powder had a moisture content of <3.0%.

TABLE 4

| Nutritional composition recipe | |
| --- | --- |
| Ingredient | Amount added (kg/ 100 kg final products) |
| Added to evaporated composite blend: | |
| Fat blend | 13.4 |
| Potassium Citrate | 0.55 |
| Calcium carbonate | 0.37 |
| Magnesium chloride | 0.21 |
| TriCalcium phosphate | 0.15 |
| Sodium citrate | 0.09 |
| Sodium chloride | 0.15 |
| Calcium hydroxide | 0.03 |
| Dry-blended: | |
| Lactose | 5.6 |
| Galacto-oligosaccharides powder | 4.4 |
| Premixes Vitamins, Trace elements, | 0.4 |

TABLE 4-continued

| Nutritional composition recipe | |
| --- | --- |
| Ingredient | Amount added (kg/ 100 kg final products) |
| Nucleotides | |
| 2'-Fucosyllactose | 0.30 |

The powdered nutritional composition was reconstituted in demineralized water at 40° C. for 60 min at a level of 13 g powder per 90 g of water. The level of casein mineralization (i.e. protein-bound calcium, PBCa/Cas) in the product was determined using the methods described above.

The nutritional composition was analyzed using the methods described hereinbefore. Casein content was determined via TN, NPN and amino acid composition as described hereinbefore. Results are indicated in Table 5.

TABLE 5

| Key characteristics of nutritional composition | | |
| --- | --- | --- |
| Total protein (6.38 * TN) | g/100 g | 11.4 |
| Casein (CN * 6.38) | g/100 g | 4.2 |
| NPN | g/100 g | 0.18 |
| NPN/TN | | 0.10 |
| Fat | g/100 g | 27 |
| 2'-FL | g/100 g | 0.25 |
| GOS | g/100 g | 3.0 |
| Lactose | g/100 g | 51.7 |
| Ca | mg/100 g | 421 |
| PBCa/Cas | mmol/10 g casein | 5.2 |

The sample was subsequently subjected to in-vitro digestion using the method described in Example 2, with samples taken at pH 6.5, 6.0, 5.5, 4.5 and 3.5. Photographic images of samples after reaching these pH values are shown in FIG. 4, SDA-PAGE electrophoretograms of are shown in FIG. 6.

As can be seen from FIGS. 5 and 6 at pH below 6.0 no large coagulates were observed and no intact casein (see range 25-35 kDa) is observed anymore, clearly indicating that under gastric conditions (pH<5) no curd formation takes place and digestion takes place effectively.

The invention claimed is:

1. A nutritional composition comprising carbohydrates, protein and a fat composition, wherein:
  (a) the nutritional composition has a total calcium content on dry matter of at least 3.5 g/kg;
  (b) the protein comprises casein;
  (c) the nutritional composition has a content of protein-bound calcium of 7.5 mmoles or less per 10 grams of casein; and
  (d) the ratio NPN to TN is 0.7 to 1.0 or less than 0.7 to 1.0, with:
    NPN meaning non-protein nitrogen in the nutritional composition in grams per 100 grams of nutritional composition (g/100 g); and TN meaning total nitrogen (TN) in the nutritional composition in g/100 g.

2. The nutritional composition according to claim 1, wherein the fat composition comprises at least 20% by weight, based on total weight of the fat composition of triacylglycerols (TAG) originating from a bovine milk fat source.

3. The nutritional composition according to claim 2, wherein the bovine milk fat source is whole milk, cream or anhydrous milk fat.

4. The nutritional composition according to claim 1, wherein the fat composition comprises:
  (a) 0.5-2.2% by weight, based on total weight of fatty acid acyl groups in TAG of butanoate groups (C4:0); and
  (b) 18.0-35.0% by weight based on total weight of fatty acid acyl groups in TAG of long chain saturated fatty acid acyl groups having a chain length of 12 or more carbon atoms at the sn-1 and sn-3 position in TAG.

5. The nutritional composition according to claim 1, which further comprises at least one human milk oligosaccharide.

6. The nutritional composition according to claim 5, wherein the at least one human milk oligosaccharide is present in an amount of 0.05 to 2.0 grams per 100 grams of the nutritional composition on dry matter.

7. The nutritional composition according to claim 1 in powder form.

8. The nutritional composition according to claim 1, wherein the fat composition comprises at least 45% by weight based on total weight of the fat composition of triacylglycerols (TAG) originating from a bovine milk fat source.

9. The nutritional composition according to claim 8, wherein the bovine milk fat source is whole milk, cream or anhydrous milk fat.

10. The nutritional composition according to claim 1, wherein the fat composition comprises:
  (a) 0.6-2.0% by weight, based on total weight of fatty acid acyl groups in TAG of butanoate groups (C4:0); and
  (b) 19.0 to 32.0% by weight, based on total weight of fatty acid acyl groups in TAG of long chain saturated fatty acid acyl groups having a chain length of 12 or more carbon atoms at the sn-1 and sn-3 position in TAG.

11. The nutritional composition according to claim 1, wherein the total calcium content on dry matter is 3.6 to 8.0 g/kg.

12. The nutritional composition according to claim 1, wherein the ratio NPN to TN is between 0.01 and 0.5.

13. The nutritional composition according to claim 5, further comprising at least a fucosylated lactose.

14. The nutritional composition according to claim 13, further comprising 2'-fucosyllactose.

* * * * *